United States Patent [19]

Wilbur et al.

[11] Patent Number: 4,870,188

[45] Date of Patent: Sep. 26, 1989

[54] VINYL SUBSTITUTED RADIOHALOGEN CONJUGATES FOR PROTEIN LABELING

[75] Inventors: Daniel S. Wilbur, Edmonds; Stephen W. Hadley, Seattle, both of Wash.

[73] Assignee: NeoRx Corporation, Seattle, Wash.

[21] Appl. No.: 39,155

[22] Filed: Apr. 16, 1987

[51] Int. Cl.$^4$ .................. C07D 207/46; C07C 69/76; C07C 69/62; A61K 49/02

[52] U.S. Cl. .................. 548/542; 560/104; 560/219; 424/1.1

[58] Field of Search ............... 424/1.1; 560/219, 104; 548/542

[56] References Cited

U.S. PATENT DOCUMENTS

| | | | |
|---|---|---|---|
| 3,412,162 | 11/1968 | Musgrave | 560/104 X |
| 3,891,695 | 6/1975 | Ray-Chaudhuri et al. | 560/219 X |
| 4,450,149 | 5/1984 | Kabalka . | |
| 4,524,059 | 6/1985 | Elmaleh et al. . | |
| 4,541,957 | 9/1985 | Nakatsuka et al. . | |
| 4,725,426 | 2/1988 | Hofmeister et al. | 424/1.1 |
| 4,755,323 | 7/1988 | Eidenschink et al. | 252/299.61 |

FOREIGN PATENT DOCUMENTS

| | | | |
|---|---|---|---|
| 0053638 | 5/1978 | Japan | 560/104 |
| 0152830 | 9/1983 | Japan | 560/219 |

OTHER PUBLICATIONS

Goodman, M. M. et al., Design, synthesis and evaluation of 2-deoxy-2-iodovinyl-branched carbohydrates as potential brain imaging agents, Proceedings of the Sixth International Symposium on Radiopharmaceutical Chemistry, Boston, Mass, Jun. 29-Jul. 3, 1986, in Journal of Labelled Compounds and Radiopharmaceuticals 23:243-245, 1987.

Seyferth, D., "Vinyl Derivatives of the Metals. III. Vinylmercuric halides," The Journal of Organic Chemistry 22:478, 1957.

Hanson, R. N. et al., E-17α-[$^{125}$I]iodovinylestradiol: an estrogen–receptor–seeking radiopharmaceutical, J. Nucl. Med. 23(5):431-436, 1982.

Hanson, R. N., et al., Synthesis and evaluation of potential radioligands for the progesterone receptor, J. Med. Chem. 28(11):1695-1699, 1985.

Hoyte, R. M. et al., Snythesis and evaluation of potential radioligands for the progesterone receptor, J. Med. Chem. 28(11):1695-1699, 1985.

R. N. Hanson, D. E. Seitz, and J. C. Botarro, "E-17-[1-25I]Iodovinylestradiol: An Estrogen–Receptor–Seeking Radiopharmaceutical"*J. Nucl. Med.* 23(5):431-436, 1982.

Jerry March, *Advanced Organic Chemistry, Reactions, Mechanisms, and Structure*, Third Edition, John Wiley & Sons, 1985.

M. M. Goodman, A. P. Callahan, and F. F. Knapp, Jr., *Design, Synthesis and Evaluation of 2-Deoxy-2-Iodovinyl-Branched Carbohydrates As Potential Brain Imaging Agents*, Nuclear Medicine Group, Oak Ridge National Laboratory, Oak Ridge, Tenn., 37831, Paper 106, pp. 243-245.

(List continued on next page.)

Primary Examiner—John S. Maples
Attorney, Agent, or Firm—Christensen, O'Connor, Johnson & Kindness

[57] ABSTRACT

Vinyl radiohalogenated small molecules as shown in formulas I and II:

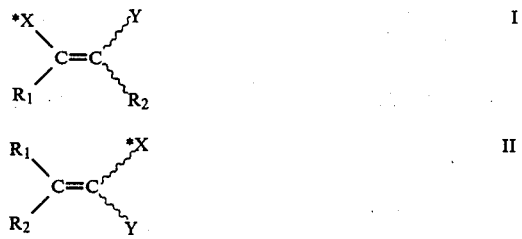

wherein *X is a radiohalogen, C=C is a double bonded set of sp$^2$ hybridized carbon atoms, and substituents R$_1$, R$_2$, and Y are as defined below. R$_1$ and R$_2$ are substituents independently selected from among hydrogen; alkyl or substituted alkyl, provided that any sp$^2$ or sp carbon atom substituted on the alkyl is separated from C=C by at least one fully substituted sp$^3$ carbon atom; aryl or substituted aryl, provided that the aryl is bonded directly to C=C; heteroalkyl, provided, first, that no heteroatom of the heteroalkyl bonds directly to C=C and, second, that any sp$^2$ or sp hybridized carbon bonded to a heteroatom of the heteroalkyl is not bonded directly to or otherwise conjugated with C=C and, third, that where a single sp$^3$ carbon intervenes between C=C and an sp$^2$ or sp carbon bonded to a heteroatom that intervening sp$^3$ carbon must be fully substituted; heteroaryl, provided that a heteroatom of the heteroaryl is not bonded directly with C 50 C; mixed alkylaryl, provided first, that no heteroatom is bonded to C=C and, second that either an aryl moiety of the mixed alkylaryl is directly bonded to C=C or that any aryl moiety is separated from C=C by at least one sp$^3$ carbon atom and, where only one sp$^3$ hybridized carbon atom intervenes between C=C and an aryl moiety, that intervening sp$^3$ carbon must be fully substituted. Y is substituent containing any of the groups described above for R$_1$ and R$_2$, except that Y cannot be hydrogen, and bearing a functional group suitable for binding to protein under conditions that preserve the biological activity of the protein. The compounds of formulas I and II can be coupled to proteins such as monoclonal antibodies ot provide reagents for diagnostic and therapeutic applications.

Also metalated precursors of compounds I and II, as well as radiophormaceutical reagent kits containing any of the subject small molecules.

2 Claims, No Drawings

OTHER PUBLICATIONS

L. E. Salisbury, "Kinetic Study of the Relationship of Rearrangement to Racemization in Certain Dibenzo[a,e] cyclooctatetraenes," *J. Org. Chem.* 43(26):4991–4995, 1978.

J. Schwartz and J. A. Labinger, "Hydrozirconation: A New Transition Metal Reagent for Organic Synthesis," *Agnew Chem. Int. Ed. Engl.* 15(6):333–340, 1976.

D. Seyferth, "Vinyl Derivatives of the Metals. III. Vinylmercuric Halides," Department of Chemistry, Harvard University, Cambridge 38, Mass.

R. C. Larock, S. K. Gupta, H. C. Brown, "Reaction of 2-Alkenyl-1,3,2-benzodioxaboroles with Mercuric Acetate. A Convenient Stereospecific Procedure for the Conversion of Alkynes into Alkenylmercuric Salts," *J. Amer. Chem. Soc.* 94, pp. 4371–4373, (1982).

G. W. Kabalka, E. E. Gooch, H. C. Hsu, L. C. Washburn, T. T. Sun, and R. L. Hayes, "Rapid and Mild Synthesis of Radioiodinated Estrogen Derivatives Via Organoborane Technology," *Applications of Nuclear and Radiochemistry*, Edited by Richard M. Lambrecth and Nabil Morcos, Brookhaven National Laboratory, Pergamon Press, Chapter 17, pp. 197–203.

G. W. Kabalka, E. E. Gooch and H. C. Hsu, "A Convenient Procedure for the Synthesis of Vinyl Iodides Via the Reaction of Iodine Monochloride with Vinylboronic Acids," *Synthetic Communications* 11(3):247–251, 1981.

VINYL SUBSTITUTED RADIOHALOGEN CONJUGATES FOR PROTEIN LABELING

TECHNICAL FIELD

This invention relates to radiohalogenated small molecules for labeling proteins, particularly antibodies, useful for clinical diagnosis and therapy, and to methods of introducing high specific activity radiohalogens into protein molecules.

BACKGROUND OF THE INVENTION

Radiohalogenated proteins have been the object of extensive scientific study and promise to be useful for a variety of clinical applications, both in vitro and in vivo. For example, radioiodinated ferritin is used in an in vitro diagnostic determination of ferritin concentration in serum. Radioiodinated thyroid stimulating hormone is employed in a similar assay.

Radionuclides of halogens possess properties that make them very attractive for both diagnostic imaging and radiotherapy. For example, radioiodine as iodine-123 ($T\frac{1}{2} = 13$ h, 159 keV gamma, electron capture) is nearly ideal for imaging with the current gamma cameras, and iodine-131 ($T\frac{1}{2} = 8$ d, 364 keV gamma, beta particle), while producing images of lower quality, has been demonstrated to be useful in clinical radiotherapy of the thyroid. Similarly, bromine radionuclides such as bromine-75 ($T\frac{1}{2} = 1.6$ h, positron) and bromine-76 ($T\frac{1}{2} = 16$ h, positron) have properties that make them attractive for positron tomographic imaging, and bromine-77 ($T\frac{1}{2} = 2.4$ d, several gammas, electron capture) has properties that make it attractive for radiotherapy. Other radiohalogens, such as fluorine-18 ($T\frac{1}{2} = 110$ min, positron) and astatine-211 ($T\frac{1}{2} = 7.2$ h, alpha particle), are also attractive candidates for radioimaging and radiotherapy.

The development of monoclonal antibodies that localize in cancerous tissue due to their high specificity and affinity for antigens on tumor cell surfaces has increased the prospect of clinical applications of radiolabeled antibodies for diagnosis and/or therapy. The high specificity of the antibodies make them desirable candidates as carrier molecules to which specific radionuclides may be attached for delivering radioactivity to a cancer site.

Other proteins, protein fragments, modified proteins, and peptides that tend to concentrate in an organ or diseased tissue are likewise candidates to be radiohalogenated. For example, radiohalogenated fibrinogen could be used to localize deep vein thrombosis by in vivo imaging. Disease-altered uptake of pituitary and other peptide hormones could be monitored in a similar manner.

Unfortunately, there are presently no routine clinical diagnostic or therapeutic applications of radiohalogen labeled antibodies for use in vivo. Direct radiohalogen labeling of antibodies and other proteins has proved to be difficult. Antibodies exhibit varying sensitivities to radiolabeling reaction conditions, and the oxidizing reaction conditions necessary for standard radiohalogenations are particularly deleterious. Direct radioiodination of proteins has become routine, but very often a measurable reduction of biological activity of the protein results. The stability of the attached radiolabel can also vary. For example, the loss of radioiodine from antibodies has been found to be as high as 50% in 24 hours for some labeled antibodies. Radiobrominations require even stronger oxidizing reaction conditions than radioiodinations, and attempts to radiobrominate proteins directly have met with little success unless expensive and difficult to obtain enzymes are used as oxidants. Furthermore, direct radiohalogenation of proteins occurs primarily at tyrosyl residues, and the activated phenol ring of tyrosine contributes to an inherent electronic instability of the resultant ortho-substituted radiohalogen label. The radiohalogen label is also subject to steric hindrance effects and may in addition be available to deiodinase enzymes which catabolize the structurally similar thyroid hormones, e.g., thyroxine.

One approach that circumvents subjecting proteins to the harsh reaction conditions necessary for direct radiohalogenations is the use of small molecules that can be radiolabeled in a separate reaction vessel and subsequently coupled to proteins under mild reaction conditions. This approach is the basis of the commercially available Bolton-Hunter reagent, N-succinimidyl-3-(4-hydroxyphenyl)propionate. Moderate radiolabeling yields are thereby obtained with radioiodine (35–60% yields of labeled proteins), but the stability of the radioiodine label suffers from the same problems as described for the chemically similar radioiodinated tyrosyl residues. Similarly, the commercially available Wood's reagent, methyl-4-hydroxybenzimidate, can be radioiodinated prior to attachment to proteins. However, the radioiodinated product is also plagued with the inherent instability of the ortho-iodinated phenol. Even though these reagents do not yield as stable as radiolabel as desirable, they have been extensively used for radioiodination because little deactivation of the protein results from their use.

The phenolic ring is employed in both the Bolton-Hunter and Wood's reagents because an activated aromatic ring is required in order to introduce high specific activity radioiodine into these molecules. It would be very desirable to be able to introduce radiohalogens into other small molecules so that the radiolabel would be more stably attached.

Recent reports in the literature describe the use of organometallic intermediates to introduce high specific activity radiohalogens into vinyl positions on alkene moieties. For example, vinylstannanes have been reportedly used to radiohalogenate steroid in the 17 position (Hanson, R. N., et al., J. Nucl. Med. 23: 431–436, 1982), and to label sugars (Goodman, M. M., et al., in Sixth International Symposium on Radiopharmaceutical Chemistry, Boston, MA, June 29–July 3, 1986, paper number 106). Use of vinyl boronic acids in the radiohalogen labeling of steroids has also been reported. Kabalka, G. W., et al., Synth. Commun. 11: 247–251, 1981; Kabalka, G. W., et al., Applications of Nuclear and Radiochemistry, Lambrecht, R. M., et al., Eds., Pergamon Press, Newark, N.J., Chapter 17, pp. 197–203, 1981.

SUMMARY OF THE INVENTION

This invention provides vinyl radiohalogenated small molecules that can be bonded to proteins such as monoclonal antibodies under conditions that preserve the biological activity of the protein. The stability of the bond between the radiohalogen and the carbon carbon double bond to which it is attached is maintained by selecting the other substituents of the alkene so as to prevent the double bond from migrating to other positions in the molecule. The other substituents of the alkene are also selected to prevent addition to the double bond when the radiolabeled protein conjugate is introduced into a physiological milieu. Enhanced stability of the radiolabel results. The subject radiohalogenated small molecules are shown in formulas I and II:

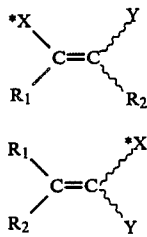

wherein *X is a radiohalogen, C=C is a double bond set of sp² hybridized carbon atoms, and substituents $R_1$, $R_2$, and Y are as defined below.

$R_1$ and $R_2$ are substituents independently selected from among hydrogen; alkyl or substituted alkyl, provided that any sp² or sp carbon atom substituted on the alkyl is separated from C=C by at least one fully substituted sp³ carbon atom; aryl or substituted aryl, provided that the aryl is bonded directly to C=C; heteroalkyl, provided, first, that no heteroatom of the heteroalkyl bonds directly to C=C and, second, that any sp² or sp hybridized carbon bonded to a heteroatom of the heteroalkyl is not bonded directly to or otherwise conjugated with C=C and, third, that where a single sp³ carbon intervenes between C=C and an sp² or sp carbon bonded to a heteroatom that intervening sp³ carbon must be fully substituted; heteroaryl, provided that a heteroatom of the heteroaryl is not bonded directly with C=C; mixed alkylaryl, provided, first, that no heteroatom is bonded to C=C and, second, that either an aryl moiety of the mixed alkylaryl is directly bonded to C=C or that any aryl moiety is separated from C=C by at least one sp³ carbon atom and, where only one sp³ hybridized carbon atom intervenes between C=C and an aryl moiety, that intervening sp³ carbon must be fully substituted.

Y is a substituent containing any of the groups described above for $R_1$ and $R_2$, except that Y cannot be hydrogen, and bearing a functional group suitable for binding to protein under conditions that preserve the biological activity of the protein. The compounds of formulas I and II can be coupled to proteins, protein fragments, immunological binding partners such as monoclonal antibodies and antibody fragments, plasma proteins, peptides, and mixtures thereof to provide reagents for diagnostic and therapeutic applications.

Also provided are metalated precursors of the foregoing radiohalogenated small molecules, as well as radiopharmaceutical reagent kits containing the subject radiolabeled and metalated small molecules.

DETAILED DESCRIPTION OF THE INVENTION

Vinyl halide bonds are as strong or stronger than arylhalide bonds and are stronger than alkylhalide bonds. The relative stability of vinyl-halogen and aryl-halogen bond results from attachment of the halogen onto an sp² hybridized carbon atom. Halogens attached to sp² hybridized carbon atoms are also much less prone to undergo nucleophilic substitution reactions than halogens attached to sp³ hybridized carbon atoms, particularly allylic and benzylic halogens; thus, the endogenous nucleophiles present in vivo are less likely to react with vinyl and aryl halides to release the anionic halide. Radiolabeled vinyl halide small molecules are therefore potential vehicles for stably attaching radiohalides onto proteins, provided that both the biological activity of the protein and the integrity of the sp² hybridized carbon atom to which the radiohalide is bonded are maintained. These requirements are achieved by the subject radiohalogenated small molecules of formulas I and II:

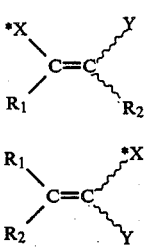

wherein *X is a radiohalogen, C=C is a double bond set of sp² hybridized carbon atoms, and substituents $R_1$, $R_2$, and Y are as defined below.

$R_1$ and $R_2$ are substituents independently selected from among hydrogen; alkyl or substituted alkyl, provided that any sp² or sp carbon atom substituted on the alkyl is separated from C=C by at least one fully substituted sp³ carbon atom; aryl or substituted aryl, provided, first, that the aryl is bonded directly to C=C and, second, that when the aryl is substituted ortho or para relative to C=C the substituent does not donate electrons to the aryl via resonance; heteroalkyl, provided, first, that no heteroatom of the heteroalkyl bonds directly to C=C and, second, that any sp² or sp hybridized carbon bonded to a heteroatom of the heteroalkyl is not bonded directly to or otherwise conjugated with C=C and, third, that where a single sp³ carbon intervenes between C=C and an sp² or sp carbon bonded to a heteroatom that intervening sp³ carbon must be fully substituted; heteroaryl, provided that a heteroatom of the heteroaryl is not bonded directly with C=C; mixed alkylaryl, provided, first, that no heteroatom is bonded to C=C and, second, that either an aryl moiety of the mixed alkylaryl is directly bonded to C=C or that any aryl moiety is separated from C=C by at least one sp³ carbon atom and, where only one sp³ hybridized carbon atom intervenes between C=C and an aryl moiety, that intervening sp³ carbon must be fully substituted. By fully substituted sp³ carbon atom as used herein is meant a carbon atom not substituted with hydrogen or any substituent such that isomerization of C=C can take place.

Y is a substituent containing any of the groups described above for $R_1$ and $R_2$, except that Y cannot be hydrogen, and bearing a functional group suitable for binding to protein under conditions that preserve the biological activity of the protein. The compounds of formulas I and II can be coupled to proteins, protein fragments, immunological binding partners such as monoclonal antibodies and antibody fragments, plasma proteins, peptides, and mixtures thereof to provide reagents for diagnostic and therapeutic applications.

As utilized herein, the symbol "*X" indicates any radioisotope of: iodine, particularly $^{123}I$, $^{125}I$, and $^{131}I$; bromine, particularly $^{75}Br$, $^{76}Br$, and $^{77}Br$; fluorine, particularly $^{18}F$; and, astatine, particularly $^{211}At$. Preferred radiohalogens *X for diagnostic imaging purposes include $^{131}I$ and most preferably $^{123}I$ for imaging with gamma cameras, and $^{18}F$, $^{75}Br$, $^{76}Br$, and $^{124}I$ for positron tomographic imaging. For clinical radiotherapy, preferred radiohalogens *X include $^{131}I$, $^{77}Br$, and $^{211}At$. Preferred radiohalogens *X for in vitro radioimmunoassay purposes include $^{125}I$ and $^{131}I$.

Symbol "C=C" indicates a double bond set of $sp^2$ hybridized carbon atoms known as an alkene. Each of the doubly bonded carbons has two additional $sp^2$ orbitals available for bonding. Radiohalogen *X bonds to one of these $sp^2$ orbitals. Symbols "$R_1$" and "$R_2$" refer to two additional vinyl substituents of the alkene, that is, to atoms or groups that are bonded to another two of the four available $sp^2$ orbitals. Substituent Y bonds to the fourth $sp^2$ orbital of C=C.

It is essential that substituents $R_1$ and $R_2$ (and also Y) do not destabilize the radiohalogen-$sp^2$ carbon bond. For example, directly bonding a heteroatom such as oxygen or nitrogen to either of the $sp^2$ hybridized carbon atoms of C=C may change the electron character of the alkene, resulting in loss of the radiohalogen. Some heteroatoms may be suitable for bonding directly to group C=C provided that the heteroatom does not donate nonbonding electrons to C=C. Examples of such heteroatoms include nitrogen when bonded to another functional group such as carbonyl that will delocalize the nonbonding electrons, e.g., a nitrogen in an amide bond. Thus, the substituents $R_1$ and $R_2$ may be heteroalkyl or heteroaryl groups, but is preferred that a heteroatom is not directly bonded to group C=C. It is also particularly important that vinyl substituents $R_1$ and $R_2$ do not render the alkene susceptible to nucleophilic addition. Examples of such nucleophilic addition to C=C include additions to α, β-unsaturated carbonyl compounds in reactions known as Michael-type additions, as defined in March, J., Advanced Organic Chemistry, 3rd edition, John Wilex & Sons, New York, NY 664–666, 1985, which is hereby incorporated by reference. Thus, for heteroalkyl groups, any $sp^2$ or sp carbon bonded to a heteroatom must not be bonded directly to or otherwise conjugated with C=C. Furthermore, where a single $sp^3$ hybridized carbon atom intervenes between C=C and an $sp^2$ or sp carbon that is bonded to a heteroatom, that $sp^3$ carbon must be fully substituted so that an isomerization of the C=C double bond is not possible. Otherwise, protons bonded to a $sp^3$ carbon atom α to the heteroatom and allylic to group C=C would be acidic, leading to activation of group C=C and migration of that double bond, which would produce the highly undesirable allylic radiohalogenated small molecule.

It is also important that $R_1$ and $R_2$ be inert toward biological molecules under physiological conditions. For example, reducing sugars would not be suitable $R_1$ and $R_2$ substituents, because such noninert substituents might lead to nonspecific glycosylation and radiolabeling of nontargeted tissues in vivo.

Permissible alkyl substituents $R_1$ or $R_2$ include protons and branched, straight-chain, or cyclic alkyl groups containing from 1 to about 12 carbon atoms that are preferably substituted with protons or methyl groups. Most preferably, $R_1$ and $R_2$ are individually selected from among protons and methyl groups. Permissible heteroalkyl substituents $R_1$ or $R_2$ include, but are not limited to, those in which the alkyl moiety either is substituted with substituents from the group halogen, OH, OG, O$_2$CG, CO$_2$G, CONH$_2$, CONG, CONHG, NH$_2$, NG$_2$, NHG, SH, SR, SOG, SO$_2$G, SO$_2$NG$_2$, SO$_2$NH$_2$, and SO$_2$NHG or which contain as linking groups —O—, —NH—, —NG—, —CO—, —CO$_2$—, —CONH—, —CONG—, —S—, —SO—, —SO$_2$—, —CO$_2$NH—, and —SO$_2$NG—, wherein G is selected from alkyl of from 1 to about 8 carbon atoms, alkenyl of from 1 to about 8 carbons, and aryl.

Permissible aryl substituents $R_1$ and $R_2$ include, but are not limited to, 5, 6 and 7 carbon aromatic rings, with the most preferable aryl substituent being phenyl. Permissible polynucleararyl substituents $R_1$ and $R_2$ include those having up to 3 aryl rings, with each ring containing 5, 6, or 7 carbon atoms. Permissible heteroaryl substituents $R_1$ and $R_2$ include, but are not limited to, 5, 6 and 7 member rings containing from 1 to about 3 heteroatoms selected from O, S, and N, with the most preferable heteroaryl substituent being pyridine. The foregoing aryl, polynucleararyl, and heteroaryl groups may be substituted with as many as 3 ionizable groups such as nitro, sulfonic acid, carboxylic acid, and amino in order to aid in the solubilization of compounds I and II in aqueous solutions. The aryl, polynucleararyl, and heteroaryl substituents $R_1$ and $R_2$ may also be substituted with alkyl and with heteroalkyl groups containing heteroatoms such as oxygen, nitrogen, and sulfur.

Vinyl substituents $R_1$ and $R_2$ of the alkene may also be a mixed alkylaryl having one or more $sp^3$ carbon atoms linking group C=C to an aromatic moiety. As described above, if there is only one intervening $sp^3$ carbon, that carbon must be fully substituted since mild base treatment of benzylic protons (which are acidic) may lead to migration of the double bond thereby destroying the radiohalogen-$sp^2$ carbon bond. The aryl moiety of mixed alkylaryl substituents R may be either carbocyclic or heterocyclic.

The symbol "Y" represents any substituent that meets the following two requirements: First, the Y substituent, being a vinyl substituent of the alkene, must not highly activate group C=C as described above with respect to substituents $R_1$ and $R_2$. Accordingly, Y may contain any of the disclosed $R_1$ and $R_2$ substituents, except hydrogen, linked to C=C. Second, the Y substituent bears a functional group (hereinafter termed "Z") that is available for bonding to protein under mild conditions, such as acylation or aminidination, that preserve the biological activity of the protein.

Functional group Z may be any activated functional group reactive with nucleophilic groups on a protein, protein fragment, antibody, antigen binding fragment, amino acid polymer, plasma protein, peptide hormone, or mixtures thereof. By "activated functional group" is meant a Z substituent that is capable of reacting with and conjugating to a nucleophilic substituent on a biologically active protein in aqueous solution at a relatively rapid rate, under reaction conditions such as temperature and pH that do not denature or otherwise impair the biological activity of the conjugated protein. Z is preferably a phenolic or imide ester, for covalent attachment to nucleophilic functional groups (or attachment sites) on amino acids or carbohydrate residues of proteins or linking molecules that can in turn be bonded to protein molecules. By "linking molecules" is meant bifunctional conjugating reagents such as amino acid polymers, carbohydrates, dicarboxylic acids, diamines, and polyalcohols.

Alternatively, functional group Z may be a nucleophilic group suitable for bonding with a derivatized protein or protein fragment containing an activated functional group. Derivatized proteins reactive with nucleophilic functional groups Z include proteins that have been reacted with cross-linking reagents such as homobifunctional imidoesters, homobifunctional N-hydroxysuccinimide (NHS) esters, and heterobifunctional cross-linkers having reactive functional groups selected from NHS esters, maleimide, pyridyl disulfides, and activated halogens such as α-keto halides. Such cross-linking reagents are commercially available from, e.g., Pierce Chemical Company, Rockford, IL. Accordingly, functional group Z may be an aldehyde, thiol, amine, carboxylate, alcohol, diazo, or groups reactive with a Michael-type acceptor containing at least one α,β-unsaturated carbonyl such as a maleimide.

Generally, it is preferred that Y (as well as $R_1$ and $R_2$) be a short-chain substituent since it is believed that unattached or cleaved radiohalogenated short-chain molecules are more rapidly removed by the kidneys. Thus, Y should preferably be a short-chain substituent having an overall molecular length equivalent to no more than about 5, and most preferably no more than 3, straight-chain carbon atoms. Such a short-chain Y may contain any of the suitably sized alkyl, heteroalkyl, aryl, heteroaryl, or mixed alkylaryl groups specified above for $R_1$ or $R_2$. Alternatively, for certain applications, Y may contain a longer spacer group between C=C and the functional group Z for protein conjugation. Examples of such elongated spacer groups include, but are not limited to, polypeptides and polysaccharides.

Representative radiohalogenated small molecules of this invention containing Z groups are represented by formulas III and IV:

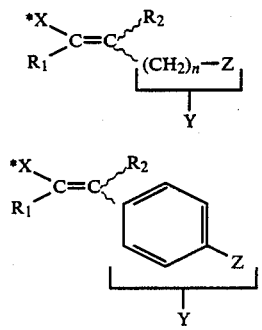

wherein radiohalogen *X is substituted on C=C in either the cis, trans, or geminal (not shown) orientation with respect to substituent Y. The integer "n" is preferably 3 through 5. Suitable functional groups Z for the above-stated purpose include phenolic esters (e.g., paranitrophenyl or tetrafluorophenyl ester), imide esters (e.g., succinimide ester), imidate esters, anhydrides, acylsuccinimides, diazo, hydrazines, alkyl halides (e.g., benzyl halide), and other groups that can be used to attach the molecule to a protein through a covalent bond. Preferred Z groups include imide ester, alkyl imide esters, amido alkyl imide esters, imidate ester, alkyl imidate esters, amido alkyl imidate esters, and Michael-type acceptors such as maleimides.

Also provided are radiohalogenated small molecules of formulas I and II wherein the Y substituent bears a precursor of the Z functional group. Suitable precursors include: carboxylic acid where Z is phenolic ester, imide ester, anhydride, acylsuccinimide, or maleimide; nitrile where Z is imidate ester; alcohol where Z is aldehyde; halide where Z is isothiocyanate, thiol, hydrazine, or amine; and amine where Z is diazo or maleimide.

While the spacer component $(CH_2)_n$ is indicated in formula III, the spacer component in Y can be selected from the permissible $R_1$ and $R_2$ substituents having equivalent lengths of up to about 12 but preferably no more than about 5 straight-chain carbon atoms. Most preferably, no more than three straight-chain carbon atoms separate functional group Z from the vinyl group, i.e., n=1, 2, or 3, in order to quickly clear background activity (any radiolabeled small molecule not attached to an antibody) for diagnostic imaging, and to minimize radiation dosage to nontargeted tissues.

In a most preferred embodiment, substituent Y has a fully substituted carbon atom directly bonded to C=C. This arrangement sterically hinders nucleophilic substitution on C=C, prevents migration of the double bond, and renders the spacer group relatively unavailable to enzymatic degradation. A representative molecule of this type has the formula:

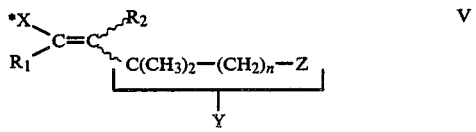

wherein *X, $R_1$, $R_2$, n, and Z are as stated above. The spacer component $(CH_2)_n$ of substituent Y may alternatively be aryl, polynucleararyl, or heteroaryl.

Illustrative but nonlimiting examples of the subject radiohalogenated small molecules include:

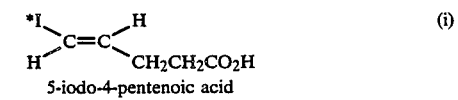

5-iodo-4-pentenoic acid

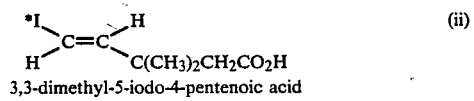

3,3-dimethyl-5-iodo-4-pentenoic acid

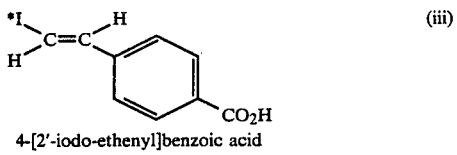

4-[2'-iodo-ethenyl]benzoic acid

It is preferred that compounds having carboxyl groups as shown above be bonded to activated functional groups (e.g., succinimide ester or tetrafluorophenyl ester) to facilitate bonding of the radiohalogenated small molecules to polypeptides, proteins, and protein fragments under conditions that preserve the biological activity of the protein component of the conjugate. The above radiohalogenated small molecules are also suitable, as shown, for direct reaction with polypeptides, proteins, and protein fragments that have been derivatized with bifunctional cross-linking reagents as described above.

Also provided are organometallic intermediate molecules of formulas VI or VII:

-continued

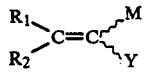  VII wherein M is a metal-containing (metalated) group suitable for transmetalation or radiohalodemetalation, as described below, and $R_1$, $R_2$, Y, and C≡C are as defined above. M is suitably a trialkyl stannane such as $Sn(n-Bu)_3$ or $SnMe_3$, wherein Bu is butyl and Me is methyl, or is selected from among HgX, (X being Cl, Br, or I), HgOAc, (OAc being acetate), $B(OH)_2$, $BX_2$, $BQ_2$, (Q being hydride, alkyl, or alkoxy containing no more than about five, and preferably fewer, carbon atoms), $Zr(cp)_2Cl$, (cp being cyclopentadienyl), and $SiF_5K_2$. Illustrative but nonlimiting examples of the subject organometallic intermediate molecules include:

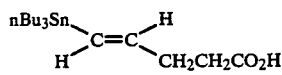  (vi)

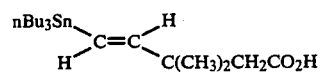  (v)

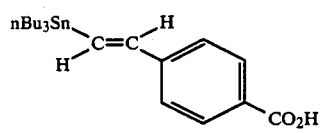  (vi)

The compounds of formulas VI and VII can be prepared by a number of methods, including hydrometalating the corresponding alkynyl precursor, substituting an organometallic group for a halogen on the corresponding vinyl halide precursor, or transmetalating the corresponding vinyl metal or organometallic compound. Compounds suitable for hydrometalating alkynyl precursors include: $LiAlH_4$, $(alkyl)_2AlH$, tri-n-butyltinhydride, $SnMe_3H$, $Cl_3SiH$, and $Zr(cp)_2HCl$.

Two general methods are provided for synthesizing the compounds of formulas iv, v, and vi. The first method employs a hydrometalation reaction to metalate an alkynyl derivative bearing the functional group of Y or a precursor thereof. For example, the alkynyl derivative bearing the functional group of Y corresponding to compound iv above would be:

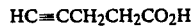  (vii)

and a commercially available alkynyl derivative (Aldrich Chemical Co., Milwaukee, WI) bearing a precursor to the functional group of Y corresponding to compound iv above would be:

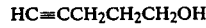  (viii)

Furthermore, the alkynyl derivative bearing an activating functional group Z of the Y substituent in vii would be:

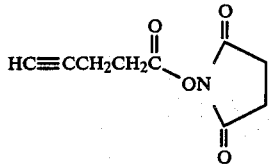  (ix)

Any of these compounds may be hydrometalated; however, it is preferred to hydrometalate compound ix with $(n-Bu)_3SnH$ to produce the activated form of compound iv above.

The second synthesis method, termed a transmetalation reaction, employs the site-specific conversion of one vinyl metal derivative into another vinyl metal derivative. Vinyl metal derivatives can be transmetalated with one of the following groups: $Sn(n-Bu)_3$, $SnMe_3$, or other trialkyl stannanes, $HgX_2$, $Hg(OAc)_2$, $BX_3$, $BQ_3$, $Zr(cp)_2Cl$, or $SiX_4$, wherein X is Cl, Br, or I, cp is cyclopentadienyl, OAc is acetate, and Q is hydride, alkyl, or alkoxy. In certain cases the transmetalated compound is too reactive for effective radiohalogenation. These metalated compounds can be converted to less reactive organometallic compounds which may be used for radiohalogenations. For example,

can be converted to

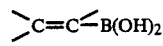

with hydroxide ion, and

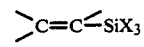

can be converted to

with KF.

Suitable precursor molecules include: 4-pentynoic acid (Aldrich Chemical Company, Milwaukee, WI); 3,3-dimethyl 4-pentynoic acid (Helvetica Chimica Acta 51: 1663–1678, 1968); and 4-ethynyl benzoic acid (J. Org. Chem. 43: 4491–4495, 1978).

Synthesis of vinylstannanes can be carried out via any one of the following two distinctly different reactions. In the first reaction, the alkynyl derivative is reacted with tri-n-butyltin hydride at 60° C. or at room temperature in the presence of a radial initiator, such as AIBN (2,2-azobis(2-methylpropionitrile)). In the second reaction, a vinyl halide derivative, which can be prepared from the corresponding alkynyl derivative, is reacted with n-butyl lithium at near −100° C. or with magnesium at room temperature, followed by reaction of the vinyl metal with a halide derivative of a trialkyltin reagent, preferably tri-n-butyltin chloride.

Synthesis of vinyl zirconium derivatives can be carried out by a hydrozirconation reaction of the alkynyl derivative using the zirconium hydride, $(cp)_2ZrHCl$, as described in Angew. Chem. Int. Ed. Engl. 15: 333–340, 1976. Similarly, synthesis of vinyl boronic acid derivatives can be a hydroboration reaction of the alkynyl derivative, preferably using catechol borane, diborane, or $BHCl_2$, followed by hydrolysis.

Synthesis of the vinyl pentafluorosilicates can be carried out by any one of the following two distinctly different reactions. In the first reaction, the alkynyl derivative is hydrosilylated with trichlorosilane, followed by treatment of the intermediate vinyl trichlorosilyl derivative with potassium fluoride. In the second reaction, a vinyl halide derivative is reacted with n-butyl lithium at near $-100°$ C. or with magnesium at room temperature, followed by reaction of the vinyl metal with silicon tetrachloride. The resulting vinyl trichlorosilyl derivative is converted to the corresponding vinyl pentafluorosilicate as described above.

The preferred method for the synthesis of the vinyl mercurial derivatives is by transmetalation of either the above vinylstannanes or vinyl boronic esters. Reaction of a vinylstannane with $Hg(OAc)_2$ yields the corresponding vinyl-HgOAc derivative in a site-specific substitution. J. Org. Chem. 22: 478, 1957. Likewise, reaction of a vinyl boronic ester with $Hg(OAc)_2$ yields the corresponding vinyl HgOAc. J. Am. Chem. Soc. 94: 4371–4373, 1972. The vinyl-HgOAc can be further converted to the vinyl Hg-X by reaction with halide ion (X).

Attaching the yet-to-be radiolabeled compounds to proteins will require the availability of a functional group Z, such as can be provided by conversion of a carboxylate precursor group into an ester containing a good leaving group, for example hydroxysuccinimide, or by conversion of a cyano precursor into an imidate ester. Such conversions can be considered as activating the molecule towards reaction with a corresponding functional group, such as an amino group (e.g., lysine residues), a thiol or hydroxy, (or, less preferably, a carboxylate), on a protein. Since metal hydrides, notably trialkyltin hydrides and boron hydrides, are reducing agents, when these reagents are used the activated imide and imidate esters or other reduction sensitive functional groups Z can only be synthesized after the hydrometalation reaction. Making the activated imide and imidate esters or other functional group Z prior to introducing the radiohalogen avoids losses in radiochemical yields and the incorporation of radiochemical impurities that would otherwise result.

Conversion of the vinyl metalated derivatives from free carboxylic acids or their stannyl esters to N-succinimidyl esters can be accomplished prior to the radiohalogenation step, using dicyclohexylcarbodiimide (DCC) and N-hydroxysuccinimide (NHS) in anhydrous tetrahydrofuran (THF). However, synthesis of imidate esters from cyano compounds is made problematical by the acid liability of the vinyl-metal bond, particularly the vinyl-tin bond. Thus, cyano containing compounds may be converted to the imidate prior to metalation or radiohalogenation and prior to formation of the imidate ester.

The vinyl metal derivatives are radiohalogenated via a halodemetalation reaction, preferably after the functional group Z is present. Radiohalogenation of the corresponding N-succinimidyl esters will yield the desired compounds via a site-specific demetalation reaction. Due to the possibility of hydrolysis of the N-succinimidyl esters, the reactions should be carried out using conditions that will minimize the reaction time. For example, the reactants can be brought to room temperature in order to minimize the hydrolysis by shortening the demetalation reaction time. Alternatively, reaction mixtures in which the hydrolysis is relatively slow can be used. For example, addition of acetic acid to the reaction mixture significantly decreases the rate of N-succinimidyl ester hydrolysis, advantageously eliminating the short time constraints routinely encountered with, e.g., the Bolton-Hunter method.

The radiohalogenation reaction mixture should have a dilute sodium thiosulfate solution added to it prior to any purification or workup procedure. Separation of any remaining radiohalide can then be conveniently accomplished prior to or during purification of the radiolabeled protein via chromatographic separations.

The radiohalogenation reactions are preferably carried out in protic solvents such as water, methanol, ethanol, or mixtures thereof. The alcoholic solvents can be conveniently removed if needed prior to addition of the radioactive compound to the protein solution, or vice versa. Alternatively, nonprotic solvents, e.g., carbon tetrachloride, can be used for radiohalogenation, since a biphasic system may provide a convenient method of separating free radiohalide from the labeled compounds.

The radiohalogenations can be monitored and purified by radio-HPLC, for example on a reverse-phase high performance liquid chromatography column (C-18) eluted with a mixture of MeOH/1% HOAc in $H_2O$.

It is contemplated that the enhanced stability and biodistribution of small molecule radioiodinated proteins made in accordance with this disclosure will make such reagents remarkably suitable for both diagnosis and therapy.

Also provided are radiopharmaceutical kits for clinical use which include a vial or set of vials containing any of compounds I through VII, preferably bearing an activated functional group Z. Compounds VI and VII will typically be provided in combination with the appropriate buffers and other reagents such that introduction of a radiohalogen will give the desired radiohalogenated molecule. The radiohalogenated product can then be attached to protein, such as a monoclonal antibody supplied in a separate vial of the kit. The kit may also include one or more chromatographic columns or other suitable means for separating any remaining precursors and impurities from the radiohalogenated protein product.

Further provided is a method of stabilizing radiohalogens, via the subject small molecules I and II, when attached to biologically active non-protein molecules such as steroids and other hormonal molecules.

This invention is further illustrated by the following Examples.

EXAMPLE 1

Synthesis of tri-n-butylstannyl-5-(tri-n-butylstannyl)-4-pentenoate

A mixture of tri-n-butyltinhydride (2.0 equiv.) (Aldrich) and 4-pentynoic acid (1.0 equiv.) (Aldrich) is warmed to 60° C. for six hours. Kugelrohr distillation of the crude product gives tri-n-butylstannyl 5-(tri-n-butylstannyl)-4-pentenoate acid.

EXAMPLE 2

Synthesis of 2,3,5,6-tetrafluorophenyl 5-(tri-n-butylstannyl)-4-pentenoate

To a solution of tri-n-butylstannyl 5-(tri-n-butylstannyl)-4-pentenoate acid (1.0 equiv.) in anhydrous THF at room temperature is added dicyclohexyl carbodiimide (1.2 equiv) (Aldrich) and 2,3,5,6-tetrafluorophenol (1.2 equiv) (Aldrich). The resulting solution is stirred overnight. The mixture is filtered, the filtrate is concentrated, and the residue is chromatographed to provide 2,3,5,6-tetrafluorophenyl 5-(tri-n-butylstannyl)-4-pentenoate.

EXAMPLE 3

Synthesis of tri-n-butylstannyl 4-[2'-(tri-n-butylstannyl)ethenyl]benzoate

A mixture of 4-ethynylbenzoic acid (1.0 equiv.) and tri-n-butyltinhydride (1.0 equiv.) (Aldrich) is warmed to 60° C. for six hours. Kugelrohr distillation of the crude product gives tri-n-butylstannyl 4-[2'-(tri-n-butylstannyl)ethenyl]benzoate.

EXAMPLE 4

Synthesis of N-succinimidyl 4-[2'-(tri-n-butylstannyl)ethenyl]benzoate

To a solution of tri-n-butylstannyl 4-[2'-(tri-n-butylstannyl)ethenyl]-benzoate (1.0 equiv.) in anhydrous tetrahydrofuran at room temperature is added dicyclohexyl carbodiimide (1.2 equiv.) (Aldrich) and N-hydroxysuccinimide (1.2 equiv.) (Aldrich). The resulting solution is stirred overnight. The mixture is filtered, the filtrate concentrated, and the residue is chromatographed to provide N-succinimidyl 4-[2'-(tri-n-butylstannyl)ethenyl]benzoate.

EXAMPLE 5

Radioiodination of N-succinimidyl 4-[2-(tri-n-butylstannyl)ethenyl]benzoate

To a vial containing 10-50 μg (0.02-0.10 μmol) N-succinimidyl 4-[2-(tri-n-butylstannyl)ethenyl]benzoate in 50 μL 5% acetic acid/methanol is added 10 μg (0.08 μmol) N-chlorosuccinimide in 10 μL methanol. To this solution is added 10 μL $Na^{125}I$ solution (diluted in Delbecco's phosphate buffered saline; Gibco Labs) (100 μCi-2 mCi). After 3-5 minutes, 10-20 μL of a 0.72 mg/ml aqueous solution of $Na_2S_2O_5$ is added. The reaction mixture is concentrated by blowing a stream of $N_2$ gas over the top of the solution until the volume is reduced to only aqueous. This material is used directly for protein labeling experiments, as described below. Alternatively, radioiodination with iodine-131 is carried out in like manner.

EXAMPLE 6

Protein labeling with N-succinimidyl 4-(2'-iodoethenyl)benzoate

The crude aqueous solution of N-succinimidyl 4-(2'-iodoethenyl)benzoate is transferred to a vial containing buffered protein solution (pH 8.5-9), or vice versa. The conjugation is complete within 5 minutes at room temperature. The labeled protein is purified from nonconjugated radioactivity using either a gel permeation chromatography column or a small pore filtration system (e.g., Centricon ultra centrifugation).

EXAMPLE 7

Radioiodination of 2,3,5,6-tetrafluorophenyl 5-(tri-n-butylstannyl)-4-pentenoate To a vial containing 10-50 μg (0.02-0.10 μmol) 2,3,5,6-tetrafluorophenyl 5-(tri-n-butylstannyl)-4-pentenoate in 50 μL 5% acetic acid/methanol is added 10 μg (0.08 μmol) N-chlorosuccinimide in 10 μL methanol. To this solution is added 10 μL $Na^{125}I$ solution (diluted in Delbecco's phosphate buffered saline; Gibco Labs) (100 μCi-2 mCi). After 3-5 minutes, 10-20 μL of a 0.72 mg/mL aqueous solution of $Na_2S_2O_5$ is added. The reaction mixture is concentrated by blowing a stream of $N_2$ gas over the top of the solution until the volume is reduced to only aqueous. This material is used directly for protein labeling experiments as described below. Radioiodination with iodine-131 is carried out in like manner.

EXAMPLE 8

Protein labeling with 2,3,5,6-tetrafluorophenyl 5-[$^{125}$I]-iodo-4-pentenoate

The crude aqueous solution of 2,3,5,6-tetrafluorophenyl 5-[$^{125}$I]-iodo-4-pentenoate is transferred to a vial containing buffered protein solution (pH 8.5-10), or vice versa. The conjugation reaction is warmed to 37° C. for 20 minutes. The labeled protein is purified from nonconjugated radioactivity using either a gel permeation chromatography column or a small pore filtration system (e.g., Centricon ultra centrifugation).

The radiohalogenated protein products can be used for radiodiagnosis and therapy. For example, monoclonal antibodies or antigen binding fragments that are specifically reactive with tumor cell associated antigens can be radiohalogenated by this method and then used for imaging tumor cell location in the body of a mammalian subject. An amount of the radiohalogenated antibody sufficient to achieve the imaging objective is introduced, e.g., by intravenous injection, into the patient's body, and thereafter the body is scanned with a scintillation detector such as a gamma camera. Such radiohalogenated antibodies can also be introduced into the mammalian subject for the purpose of tumor radiotherapy.

Other proteins, protein fragments, modified proteins, and peptides that tend to concentrate in an organ or diseased tissue can likewise be radiohalogenated by this method and used to monitor departures from homeostasis and disease states. For example, radiohalogenated fibrinogen can be used to localize deep vein thrombosis by in vivo imaging. Disease-altered uptake of pituitary and other peptide hormones can be monitored in a similar manner.

As a further example, antibodies radiohalogenated pursuant to this disclosure can be employed in in vitro radioimmunoassays.

All of the aforementioned radiohalogenated proteins are stably radiolabeled because the radiohalogen is substituted onto a nonactivated double bond of the conjugate.

While the invention has been described in conjunction with preferred embodiments, one of ordinary skill after reading the foregoing specification will be able to effect various changes, substitutions of equivalents, and alterations to the subject matter set forth herein. Hence, the invention can be practiced in ways other than those specifically described herein. It is therefore intended that the protection granted by Letters Patent hereon be limited only by the appended claims and equivalents thereof.

The embodiments of the invention in which an exclusive property or privilege is claimed are defined as follows:

1. A compound selected from the group consisting of tetrafluorophenyl ester of 5-*X-4-pentenoic acid, tetrafluorophenyl ester of 3,3-dimethyl-5-*X-4-pentenoic acid, tetrafluorophenyl ester of 4-[2'-*X-ethenyl]benzoic acid, N-succinimidyl ester of 5-*X-4-pentenoic acid, N-succinimidyl ester of 3,3-dimethyl-5-*X-4-pentenoic acid, and N-succinimidyl ester of 4-[2'-*X-ethenyl]benzoic acid, wherein *X is a radiohalogen.

2. A compound of claim 1 wherein *X is $^{123}I$, $^{124}I$, $^{125}I$, $^{131}I$, $^{75}Br$, $^{76}Br$, $^{77}Br$, $^{18}F$ or $^{211}At$.

* * * * *

UNITED STATES PATENT AND TRADEMARK OFFICE
CERTIFICATE OF CORRECTION

PATENT NO. : 4,870,188
DATED : September 26, 1989
INVENTOR(S) : D.S. Wilbur et al.

It is certified that error appears in the above-identified patent and that said Letters Patent is hereby corrected as shown below:

| Column | Line | Error |
|---|---|---|
| [57] (abstract) | 43 | "C 50 C" should be --C=C-- |
| [57] (abstract) | 44 | "provided first," should be --provided, first,-- |
| [57] (abstract) | 50 | after "is" insert --a-- |
| [57] (abstract) | 57 | "ot" should be --to-- |
| 2 | 31 | "as", second occurrence, should be --a-- |
| 3 | 18 | "bond" should be --bonded-- |
| 4 | 24 | "bond" should be --bonded-- |
| 5 | 9 | "bond" should be --bonded-- |
| 9 | 23 | "(vi)" should be --(iv)-- |
| 10 | 61 | "radial" should be --radical-- |

[56] References Cited, Other publications, fourth listed reference
"Hanson, R.N., et al., Synthesis and evaluation of potential radioligands for the progesterone receptor, J. Med. Chem. 28(11):1695-1699, 1985." should be --Hanson, R.N., et al., Radiohalodestannylation: synthesis of $^{125}$I-labelled 17a-E-iodovinylestradiol, Int. J. Appl. Radiat. Isot. 35(8):810-812, 1984.--

Signed and Sealed this

Twenty-eighth Day of August, 1990

Attest:

HARRY F. MANBECK, JR.

*Attesting Officer*     *Commissioner of Patents and Trademarks*